United States Patent
Vermaas (10) Patent No.: US 11,981,937 B2
(45) Date of Patent: May 14, 2024

(54) LIGHT-POWERED, BIOLOGICAL METHYL LAURATE PRODUCTION FROM $CO_2$ AND WATER

(71) Applicant: Willem Vermaas, Tempe, AZ (US)

(72) Inventor: Willem Vermaas, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 37 days.

(21) Appl. No.: 16/810,658

(22) Filed: Mar. 5, 2020

(65) Prior Publication Data
US 2020/0354695 A1    Nov. 12, 2020

Related U.S. Application Data

(60) Provisional application No. 62/814,035, filed on Mar. 5, 2019.

(51) Int. Cl.
| | |
|---|---|
| *C12N 9/10* | (2006.01) |
| *C12N 1/21* | (2006.01) |
| *C12P 7/62* | (2022.01) |

(52) U.S. Cl.
CPC .............. *C12N 9/1007* (2013.01); *C12P 7/62* (2013.01); *C12Y 201/01015* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis |
| 8,465,965 | B2 | 6/2013 | Mohammed et al. |
| 8,753,840 | B2 | 6/2014 | Vermaas |
| 8,962,300 | B2 | 2/2015 | Mohammed et al. |
| 9,683,246 | B2 | 6/2017 | Mohammed et al. |
| 10,385,304 | B2 | 8/2019 | Flory et al. |
| 10,563,162 | B2 | 2/2020 | Flory et al. |
| 2011/0014683 | A1 | 1/2011 | Vermaas |
| 2013/0183732 | A1* | 7/2013 | Mancinelli ........... C12N 9/0006 435/162 |
| 2020/0224152 | A1 | 7/2020 | Vermaas et al. |

FOREIGN PATENT DOCUMENTS

WO    WO-2012125737 A2 *    9/2012    ................ C12N 1/12

OTHER PUBLICATIONS

Hu et al. (Metabolic phenotypeing of the cyanobacterium Synechocystis 6803 engineered for production of alkanes and free fatty acids, Applied Energy 102, 2013, 850-59. (Year: 2013).*
Uniprot, Accession No. P72871, 2018, www.uniport.org. (Year: 2018).*
Tong et al., Cetane number prediction of biodiesel from the composition of fatty acid methyl esters, J. Am. Oil. Chem. Soc. 88, 2011, 415-23. (Year: 2011).*
Kunjapur et al., Deregulation of S-adenosylmethionine biosynthesis and regeneration improves methylationin *E. coli* de novo vanillin biosynthesis pathway, Microb. Cell Fact. 15, 2016, 61. (Year: 2016).*
Li et al., Synthesis of vanillin from glucose, J. Am. Chem. Soc. 120, 1998, 10545-46. (Year: 1998).*
Yunus et al., Methanol-free biosynthesis of fatty acid methyl ester (FAME) in *synechocystis* sp. PCC 6803, Metabolic Eng. 57, Dec. 2019, 212-27. (Year: 2019).*
Cole-Parmer Essentials Erlenmeyer Flask, www.enviromentalexpress.com, retrieved Oct. 31, 2022. (Year: 2022).*
Granata, Dependency of Microalgal Production on Biomass and the Relationship to Yield and Bioreactor Scale-up for Biofuels: a Statistical Analysis of 60+ Years of Algal Bioreactor Data, Bioenerg. Res. Oct. 2017, 267-87. (Year: 2017).*
Douchi et al, Membrane-inlet mass spectrometry enables a quantitative understanding of inorganic carbon intake, Frontiers Microbiol. Jun. 10, 2019, 1356. (Year: 2019).*
Hauf et al, Interaction of the Nitrogen Regulatory Protein GlnB (PII) with Biotin Carboxyl Carrier Protein (BCCP) Controls Acetyl-CoA Levels in the *Cyanobacterium synechocystis* sp. PCC 6803, Front. Microbiol. Jul. 2016, 1700. (Year: 2016).*
Nawabi, P., et al. "Engineering *Escherichia coli* for biodiesel production utilizing a bacterial fatty acid methyltransferase." Applied and environmental microbiology 77.22 (2011): 8052.
Petronikolou, N., et al. "Biochemical studies of mycobacterial fatty acid methyltransferase: a catalyst for the enzymatic production of biodiesel." Chemistry & biology 22.11 (2015): 1480-1490.
Sherkanov, S., et al. "Production of FAME biodiesel in *E. coli* by direct methylation with an insect enzyme." Scientific reports 6.1 (2016): 1-10.
Thomsen, T.M. et al. "Chemoenzymatic synthesis and in situ application of S-adenosyl-L-methionine analogs." Organic & biomolecular chemistry 11.43 (2013): 7606-7610.

* cited by examiner

*Primary Examiner* — Todd M Epstein
(74) *Attorney, Agent, or Firm* — Quarles & Brady, LLP (57) ABSTRACT

The disclosure relates to the production of methyl laurate by genetically engineered photosynthetic microorganisms. In particular, provided herein are methods and compositions for producing methyl laurate from carbon dioxide and water in genetically engineered cyanobacteria and other photosynthetic microorganisms.

12 Claims, 8 Drawing Sheets

10 mM bicarbonate + dodecane     1 mM methionine     1 mM methionine

Task 1. Increasing laurate production from fixed $CO_2$
The fatty acid biosynthesis pathway is heavily regulated: requires a lot of energy and reducing equivalents. Regulation via, for example:

- GlnB (PII protein): Inhibition of ACC (acetyl-CoA carboxylase) by GlnB at low 2-OG and with non-phosphorylated PII protein  [Inactivation of *glnB*]
- Allosteric inhibition of fatty acid biosynthesis enzymes? (demonstrated in *E. coli*)  [Expression of *Synechocystis* and *E. coli fab* genes]
- Feedback inhibition upon fatty acyl-ACP accumulation?  [Overexpression of ACP]

[Expression of *tesA*]

*Combination of multiple positive genetic modifications may further boost laurate production*

For good measure, also:

Increase NADPH availability

[Overexpress *acc* genes]

FIG. 4C

Task 1. Increasing laurate production from fixed $CO_2$

Indeed, significant increases in laurate production can be achieved upon deletion of *glnB* or overexpression of foreign or native fatty acid biosynthesis genes

FIG. 5

LIGHT-POWERED, BIOLOGICAL METHYL LAURATE PRODUCTION FROM $CO_2$ AND WATER

CROSS-REFERENCE TO RELATED APPLICATIONS

This application claims the benefit of U.S. Provisional Patent Application No. 62/814,035, filed Mar. 5, 2019, which is incorporated by reference herein as if set forth in its entirety.

STATEMENT REGARDING FEDERALLY SPONSORED RESEARCH AND DEVELOPMENT

This invention was made with government support under DE-EE0007561 awarded by the Department of Energy. The government has certain rights in the invention.

BACKGROUND

Laurate and methyl laurate are important commodities with rapidly growing markets. Methyl laurate, envisioned to be the primary product (along with biomass) in the proposed project, sells for around $2,000/ton for technical purity, and for significantly more if the material is high-purity. Laurate is a little cheaper, but the global laurate market is much larger at $10 billion per year. The compounds are used for personal care products, detergents, lubricants and food additives as well as for oleochemicals. Methyl laurate currently is derived from coconut and palm kernel oil. Plantations in South East Asia currently are the predominant suppliers of these oils, but there are major concerns regarding sustainable growth of this market as these plantations typically supplant natural rainforests. Accordingly, there remains a need in the art for efficient, sustainable, and environmentally friendly methods for producing methyl laurate.

SUMMARY OF THE DISCLOSURE

Provided herein are genetically engineered cyanobacteria and methods for direct production of excreted biofuels (fatty acids or fatty acyl esters such as methyl laurate) from $CO_2$, water, and light. Novel aspects of the embodiments described herein include (1) use of fatty acid methyl transferase enzyme from *Mycobacterium marinum* to convert laurate produced by the presently described genetically modified *Synechocystis* strains, and (2) the addition of catalytic amounts of methionine to increase the rate of production of methyl laurate from $CO_2$ by several fold.

In a first aspect, provided herein is a genetically engineered *Synechocystis* sp. PCC 6803 cyanobacterium, wherein the engineered cyanobacterium has been transformed with one or more plasmid vectors comprising a first nucleotide sequence derived from *Mycobacterium marinum* and encoding a fatty acid methyl transferase (FAMT) and a second nucleotide sequence encoding a thioesterase, wherein the genetically engineered *Synechocystis* sp. PPC 6803 cyanobacterium has an increased production of methyl laurate as compared to a native *Synechocystis* sp. PCC 6803 cyanobacterium. The genetically engineered *Synechocystis* cyanobacterium can further comprise one or more nucleotide sequences encoding an enzyme of the S-adenosylmethionine (SAM) regeneration cycle.

In another aspect, provided herein is a method of producing methyl laurate in genetically modified cyanobacteria. The method can comprise or consist essentially of (a) introducing an expression cassette that comprises a *Mycobacterium marinum*-derived nucleic acid encoding a fatty acid methyl transferase (FAMT) into a cyanobacterium to obtain genetically modified cyanobacteria comprising the nucleic acid, wherein the genetically modified cyanobacteria further comprising an exogenous nucleotide sequence encoding thioesterase to enable fatty acid production; (b) culturing the genetically modified cyanobacteria under conditions in which the nucleic acid encoding FAMT is expressed and methyl laurate is produced and excreted from the genetically modified cyanobacteria; (c) contacting a dodecane layer to the cyanobacteria culture, whereby the methyl laurate collects in the dodecane layer; and (d) isolating the collected methyl laurate from the dodecane layer. The method can further comprise culturing the genetically modified cyanobacteria in the presence of exogenous methionine. The genetically modified cyanobacteria can be *Synechocystis* sp. PCC 6803 cyanobacteria.

In another aspect, provided herein is method of increasing carbon utilization of a genetically modified strain of cyanobacteria. The method can comprise or consist essentially of (a) obtaining a cyanobacterium genetically modified to produce fatty acids or fatty acyl esters; and (b) introducing into the genetically modified cyanobacterium a nucleotide sequence encoding a fatty acid methyl transferase (FAMT) and an exogenous nucleotide sequence encoding a thioesterase, whereby the resulting genetically modified cyanobacterium exhibits increased carbon utilization relative to carbon utilization of a cyanobacterium not comprising the FAMT-encoding nucleotide sequence. The nucleotide sequence encoding FAMT can be derived from *Mycobacterium marinum*. The genetically modified cyanobacterium can further comprise one or more nucleotide sequences encoding one or more SAM regeneration enzymes. The method can further comprise culturing the genetically modified cyanobacteria under conditions in which the nucleic acid encoding FAMT is expressed and methyl laurate is produced and excreted from the genetically modified cyanobacteria. The cyanobacteria can be cultured in the presence of exogenous methionine.

In a further aspect, provided herein is a genetically modified *Synechocystis* strain being capable of enhanced production of methyl laurate, wherein the strain comprises a heterologous gene encoding fatty acid methyl transferase (FAMT). The strain can be *Synechocystis* sp PCC 6803.

BRIEF DESCRIPTION OF THE DRAWINGS

FIGS. 4A-4C are (FIG. 4A) a schematic representation of a homocysteine production pathway utilizing fatty acid methyl transferase (FAMT)

DETAILED DESCRIPTION OF THE DISCLOSURE

The methods and compositions of this disclosure are based at least in part on the development of genetically modified cyanobacteria that produce easily harvestable methyl laurate in culture. In particular, provided herein are methods and compositions for direct production of methyl laurate and other methylated fatty acids from $CO_2$ and water by genetically modified cyanobacteria. The genetically modified cyanobacteria produce and excrete methyl laurate for convenient capture of the excreted produce in a dodecane overlay or in an organic layer non-miscible with water. Advantages of these methods and compositions are multifold and include, without limitation, that it is not necessary to harvest cells to collect produced methyl laurate because the product is simply excreted from the cells and that methyl laurate, in contrast to laurate, is not readily consumed by other organisms found in the growth medium, thus resulting in a more stable product. Accordingly, the methods and compositions described herein provide a sustainable source of methyl laurate that does not involve burning tropical forests. Unlike conventional biodiesel production methods, cyanobacterial-based methods for producing laurate and methyl laurate are fully sustainable and likely to be preferred over conventional methods by many palm oil consuming companies.

*Synechocystis* sp. PCC 6803, a robust cyanobacterial 'cell factory,' was previously engineered for advanced biofuel (excreted fatty acids or fatty acyl esters) production. By the introduction of exogenous nucleotide sequences encoding a thioesterase into cyanobacteria, the cyanobacteria's natural light-based photosynthesis process is harnessed to produce free fatty acids from $CO_2$ and water. The predominant fatty acid produced by such genetically modified cyanobacteria is laurate, a saturated C12 fatty acid. The modified cyanobacterium excretes the free fatty acid from the cell, thus providing a way to make free fatty acids from $CO_2$ and water in a light-catalyzed manner. It was determined that two bottlenecks in the photosynthetic biofuel production process can be addressed with further genetic modifications, namely gas-liquid $CO_2$ mass transfer and biological $CO_2$ uptake, fixation, and conservation. The methods and compositions of this disclosure provide solutions for these fundamental bottlenecks that limit essentially all photosynthetic biofuel production systems.

By coupling fatty acid biosynthesis to fatty acid methylation by the introduction of a fatty acid methylase derived from *Mycobacterium marinum*, the laurate-producing cyanobacteria excrete methyl laurate which is not readily consumed by heterotrophs present in the culture. In this manner, the methods and compositions are improved over conventional methods that are not scalable due to ready consumption of laurate by heterotrophs in the growth medium. A layer of dodecane on top of the culture can be used to harvest the produced methyl laurate, which is poorly water-miscible but which readily partitions into the dodecane layer.

Genetically Engineered Photosynthetic Organisms for Production of Esterified Fatty Acids Accordingly, in a first aspect, provided herein is a genetically engineered (genetically modified) photosynthetic organism that produces and excretes esterified fatty acids such as methyl laurate. In some cases, the genetically engineered photosynthetic organism comprises one or more exogenous nucleotide sequences encoding a fatty acid methyl transferase (FAMT), for methylation of free fatty acids. Preferably, the genetically engineered photosynthetic organism further comprises one or more transgenes encoding enzymes for production of free fatty acids or fatty acyl esters. For instance, the genetically engineered photosynthetic organism comprising an FAMT transgene can further comprise an exogenous nucleotide sequence encoding an acyl-ACP illioesterase (IL) for production of free fatty acids or fatty acyl esters. As described herein, a genetically engineered photosynthetic organism comprising such exogenous nucleotide sequences are capable of light-driven production of methyl laurate from fixed $CO_2$ and water. Since esterified medium-chain fatty acids such as methyl laurate are drop-in biodiesel, the genetically engineered photosynthetic organism of this disclosure provides an efficient means of enhanced biofuel production. In addition, esterified medium-chain fatty acids are also useful in higher-value applications, thus expanding the utility of the methods and compositions of this disclosure beyond biofuels.

As used herein, the terms "genetically engineered" and "genetically modified" are used interchangeably and refer to a cell that has been modified to comprise an exogenous or non-naturally occurring nucleic acid molecule that has been created or modified by the hand of man (e.g., using recombinant or gene editing DNA technology) or is derived from such a molecule (e.g., by transcription, translation, etc.). The terms encompass transgenic organisms. A cell that contains an exogenous, recombinant, synthetic, and/or otherwise modified polynucleotide, including one or more transgenes, is considered to be a genetically modified cell and, thus, non-naturally occurring relative to any naturally occurring counterpart. In some cases, genetically modified cells contain one or more recombinant nucleic acids. In other cases, genetically modified cells contain one or more synthetic or genetically engineered nucleic acids (e.g., a nucleic acid containing at least one artificially created insertion, deletion, inversion, or substitution relative to the sequence found in its naturally occurring counterpart). The term "transgene" as used herein refers to a gene that comprises a non-native, recombinant, or modified nucleotide sequence for introduction into a microorganism.

It will be understood that, although genetically modified cyanobacteria are exemplified herein, a variety of photosynthetic organisms can be used to produce esterified fatty acids such as methyl laurate as described herein. In some cases, the photosynthetic organism is a cyanobacterium or alga. Exemplary cyanobacteria include, without limitation, *Synechocystis* sp PCC 6803. As used herein, the term "photosynthetic organism" includes an organism, whether single or multi-cellular, capable of carrying out the photosynthetic process of harnessing light energy to induce photochemical oxidation of water molecules to generate electrons. Photosynthetic organisms include, without limitation, plants and microorganisms such as algae, cyanobacteria, and phototrophic and chemoautotrophic bacteria. As used herein, the term "photosynthetic cell" includes a single cell, whether a whole single-cellular organism or a single cell of a multicellular organism (e.g., isolated from such organism), capable of carrying out the photosynthetic process. Thus, in some instances, a photosynthetic cell is also a photosynthetic organism (e.g., a cyanobacterium).

Exemplary cyanobacteria for genetic modification as described herein include, without limitation, cyanobacteria belonging to *Synechocystis, Synechococcus, Prochlorococcus*, Acaryochloris, Cyanothece, Cyanobacterium, and *Anabaena*. In some cases, the cyanobacterium is the unicellular cyanobacterium *Synechocystis* sp PCC 6803, which is a strain of cyanobacteria that was originally isolated from a freshwater lake in 1968 and is available from ATCC as ATCC® 27184™. *Synechocystis* sp PCC 6803 cyanobacteria are highly amenable to genetic modification and demonstrate versatile carbon metabolisms, growing under photoautotrophic, mixotrophic, and heterotrophic conditions. Furthermore, genetic modifications in *Synechocystis* sp PCC 6803 cyanobacteria are quite stable. Because *Synechocystis* sp PCC6803 lacks certain acyl-CoA breakdown pathways, it may be more preferable to other photosynthetic hosts.

The FAMT encoding nucleotide sequence can be derived from *Mycobacterium marinum*. Genomic DNA for *Mycobacterium marinum* is available from genomic databases and the American Type Culture Collection (ATCC). In some cases, the transgenic cyanobacterium is obtained by introducing an expression cassette that comprises a *Mycobacterium marinum*-derived nucleic acid encoding a fatty acid methyl transferase (FAMT). Nawabi et al. (Applied and Environmental Microbiol. 2011, 77(22):8052-61) demonstrated in vivo and in vitro that a novel bacterial FAMT from *M. marinum* gene leads to FAME and 3-OH-FAME accumulation when expressed in *E. coli*.

In some cases, expression of FAMT is controlled by an operably linked promoter. Various promoters can be operably linked with a nucleic acid comprising the coding region of the gene product of interest in the vectors to drive expression of the gene product of interest in accordance with embodiments herein. As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter is capable of affecting the expression of that coding sequence (i.e., the coding sequence is under the transcriptional control of the promoter).

In some cases, the genetically modified cyanobacterium further comprises one or more exogenous nucleotide sequences encoding enzymes of the S-adenosylmethionine (SAM) regeneration cycle. Without being bound to any mechanism or theory, expression of SAM regeneration cycle enzymes may reduce or eliminate the need for exogenous methionine for high methyl laurate yield.

Any appropriate method of introducing nucleic acid sequences described herein into a photosynthetic host organism (e.g., cyanobacterium) can be used. In some cases, nucleic acids are transfected into a host cyanobacterium. The term "transfected" or "transformed" or "transduced" as used herein refers to a process by which exogenous nucleic acid is transferred or introduced into the host cell. A "transfected" or "transformed" or "transduced" cell is one which has been transfected, transformed, or transduced with exogenous nucleic acid. The term "cell" as used herein includes the primary subject cell and its progeny. In some cases, a nucleic acid as described herein is introduced into *Synechocystis* sp. PCC 6803 cyanobacteria by physiological transformation and homologous recombination or by introducing one or more plasmids capable of replicating in certain cyanobacterial strains. For example, transgenes introduced into *Synechocystis* sp. PCC 6803 cyanobacteria may be targeted to plasmid or chromosomal sites. In some cases, the FAMT gene derived from *Mycobacterium marinum* can be amplified by PCR and integrated into a plasmid comprising *Synechocystis* flanking regions, thus targeting the FAMT gene for integration into a specific site on the *Synechocystis* genome upon introduction into the host cell. In some cases, an antibiotic-resistance marker or other selection marker is used to allow for transformant selection. For example, the plasmid comprising *Synechocystis* flanking regions can further comprise one or more antibiotic-resistance markers for antibiotic-based selection of transformants.

Transformation vectors can also contain a second gene that encodes a protein that, e.g., imparts resistance to antibiotic or other selectable marker. Optionally, one or more genes can be followed by a 3' untranslated sequence containing a polyadenylation signal. Expression cassettes encoding the transgenes can be physically linked in the vector or on separate vectors.

In some cases, it may be useful to synthesize nucleic acids, either completely or in part; by methods known in the art. For example; all or a portion of nucleic acids of this disclosure may be synthesized using codons preferred by a selected host. In some embodiments, at least one of the transgenes can comprise codons preferred for expression in cyanobacteria. Species-preferred codons may be determined, for example, from the codons used most frequently in the proteins expressed in a particular host species. Other modifications of the nucleotide sequences may result in mutants having slightly altered activity.

Methods for Producing Esterified Fatty Acids

In another aspect, provided herein are methods for using a genetically modified cyanobacterium described herein for producing methyl laurate and other esterified fatty acids. In one embodiment, the method comprises obtaining a host genetically modified cyanobacterium comprising an exogenous nucleotide sequence ("transgene") encoding a thioesterase and a transgene encoding a fatty acid methyl transferase (FAMT); and culturing the transgenic cyanobacterium under conditions in which thioesterase and FAMT are expressed, whereby methyl laurate is produced and excreted from the genetically modified cyanobacterium.

In some cases, the method further comprises culturing the cyanobacteria in the presence of an exogenous methyl donor such as SAM (S-adenosylmethionine) or an enzymatically active analog thereof. For example, synthetic or semisynthetic SAM analogs could be used as methyl donors. Exemplary SAM analogs include, without limitation, those described by Thomsen et al., *Org. Biomol. Chem.*, 2013, 11, 7606-7610.

The methods provided herein can comprise cultivating methyl laurate-producing photosynthetic microorganisms under appropriate culture conditions and in an appropriate growth medium. For example, when the transgenic photosynthetic microorganism is a transgenic cyanobacterium, the transgenic cyanobacteria can be grown in enclosed bioreactors containing growth medium. Growth media suitable for culturing cyanobacteria are commercially available. In some cases, transgenic cyanobacteria are grown in enclosed ponds or other culture vessels. Culture vessels can be equipped for sampling to measure cell density, photosynthesis parameters, and for methyl laurate measurements by any appropriate technique. It will be understood that growth conditions (e.g., temperature, pH, light intensity) can be fairly variable depending on the type of culture vessel, type of microorganism, etc. In general, growth temperatures are generally between about 20° C. and about 35° C. (about 25, 26, 27, 28, 29, 30, 31, 32, 33, 34, 35° C.). In some cases, the growth temperature is about 30° C. In some cases, pH is initially around 8 but may increase to pH 10-11 during culturing. In some cases, light intensity can be up to 250 micromole photons per $m^2$ per second (s).

Increasing biofuel productivity correspondingly reduces the water or growth medium required per gallon of biofuel. *Synechocystis* can also be grown using seawater to reduce freshwater needs.

The examples demonstrate methyl laurate production at the scale of a 55 Liter photobioreactor. However, since methyl laurate is much more biologically stable than laurate, it will be understood that the methods of this disclosure are suitable for large-scale production by photosynthetic microbes.

Any appropriate method for observing methyl laurate production can be used including, without limitation, those described in the Examples. For example, gas chromatography can be used to observe methyl laurate production.

In some cases, the methods provided herein can further include capturing methyl laurate produced by the cultivated cyanobacteria. Any appropriate method of harvesting methyl laurate excreted by the transgenic cyanobacteria can be performed. As esterified medium-chain fatty acids ("biodiesel") produced by the engineered cyanobacteria of this disclosure are poorly soluble in aqueous medium, the biodiesel products may be concentrated in an organic phase on top of the culture, which helps efficient harvesting. For example, in some cases, the methyl laurate is harvested by applying an organic, biocompatible top layer that does not mix with water (e.g., dodecane, isopropyl myristate, etc.). At high levels of methyl laurate production, methyl laurate will separate from the aqueous phase even in the absence of an added organic top layer and harvesting can comprise settling and scooping off the aqueous phase. In some cases, harvesting comprises contacting an organic layer to the cyanobacteria culture, whereby the methyl laurate collects in the organic layer; and isolating the collected methyl laurate from the organic layer.

In some cases, genetically engineered photosynthetic microorganisms of this disclosure are further modified, for example, to increase laurate production from fixed $CO_2$, to decouple microorganism growth from ethyl laurate production, and/or to reduce exopolysaccharide (EPS) production.

Uses for Esterified Fatty Acids

In another aspect, provided herein are methods for using methyl laurate produced according to the methods of this disclosure. Methyl laurate produced according to the methods of this disclosure may be used to produce a wide variety of products, including biofuels, personal care products, detergents, lubricants and food additives as well as for oleochemicals and other chemicals that use methyl laurate as a precursor. The methods and compositions of this disclosure make it light-powered, biologically-based methods of methyl laurate production economically feasible, in part because a large fraction of fixed carbon is directed to production of methyl laurate.

In some cases, provided herein are methods for improved production of biofuels. As used herein, the term "biofuel" refers to any fuel that derives from a biological source. Biofuel refers to one or more hydrocarbons, one or more alcohols, one or more fatty esters, or mixtures thereof. Preferably, liquid hydrocarbons are used. As used herein, the term "hydrocarbon" generally refers to a chemical compound containing carbon (C) and hydrogen (H) (and optionally oxygen (O)). Hydrocarbons may be in gaseous, liquid, or solid form, or any combination of these forms, and may have one or more double or triple bonds between adjacent carbon atoms in the backbone. Accordingly, the term includes linear, branched, cyclic, or partially cyclic alkanes, alkenes (e.g., propene, butene, pentene, hexene, heptene, octene, nonene, decene, undecene, dodecene, tridecene, tetradecene, pentadecene, hexadecene, heptadecene, octadecene, nonadecene, eicosene, uneicosene, doeicosene, and isomers and mixtures thereof), lipids, and paraffin. The term also includes fuels, biofuels, waxes, solvents, and oils.

As used herein, the term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

The practice of the present invention will employ, unless otherwise indicated, conventional techniques of molecular biology, microbiology, and recombinant DNA, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

The Examples in the following section demonstrate production and characterization of developed a genetically modified cyanobacteria strain that efficiently converts free fatty acids to methyl esters.

Figure 1:
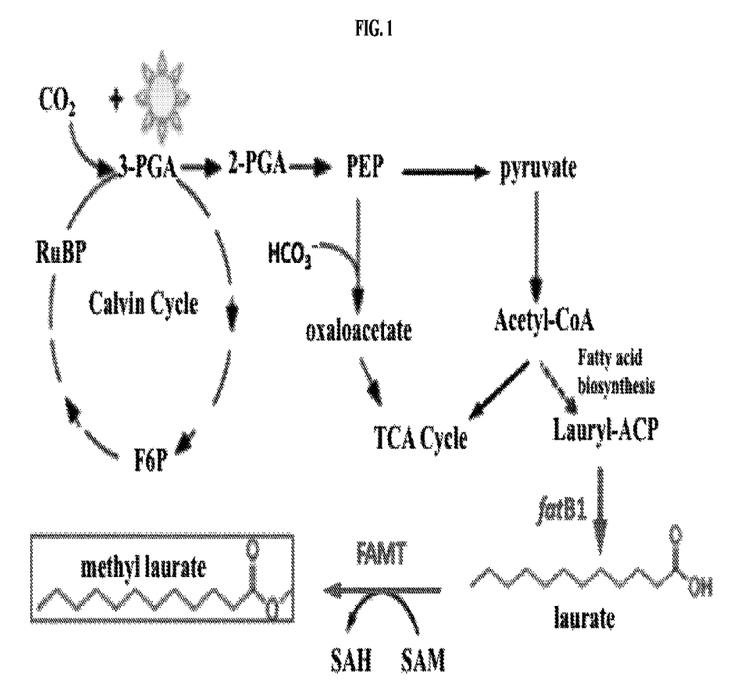
FIG. 1 illustrates the pathway by which light, water, and $CO_2$ are used for methyl laurate production in photosynthetic organisms. The introduction of fatty acid methyl transferase (FAMT) with activity toward laurate and catalytic amounts of S-adenosyl-methionine (SAM) promote efficient methyl laurate production. Advantageously, this process eliminates the requirement for an appropriate stoichiometry of produced alcohol and laurate.
Figure 2A:
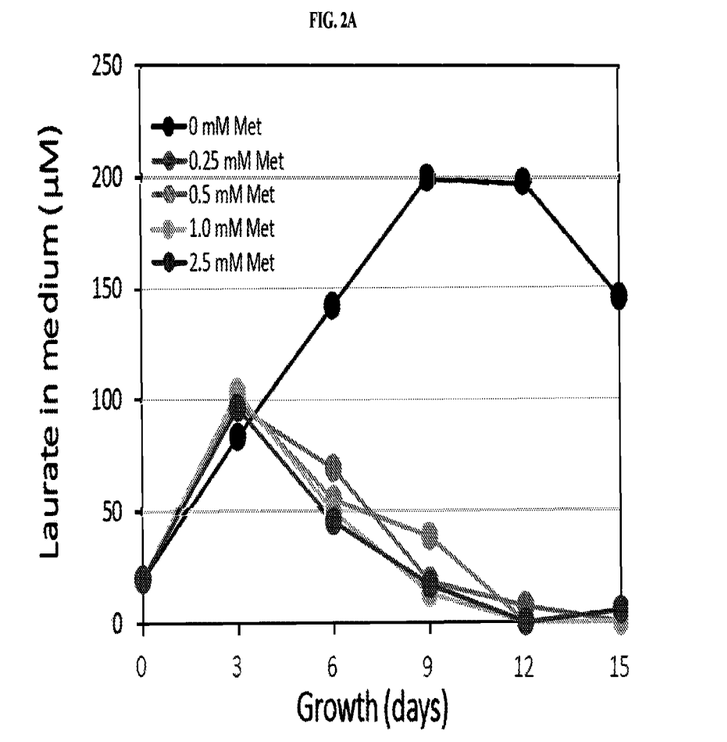
FIG. 2A demonstrates that methionine was necessary for methyl laurate production.
Figure 2B:
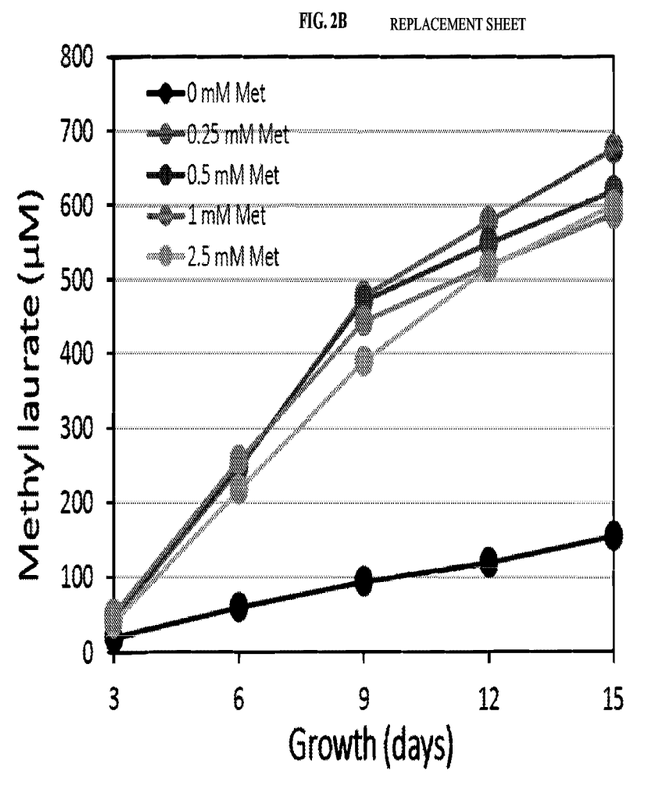
FIG. 2B demonstrates that laurate levels were depleted as methyl laurate accumulated.
Figure 3:
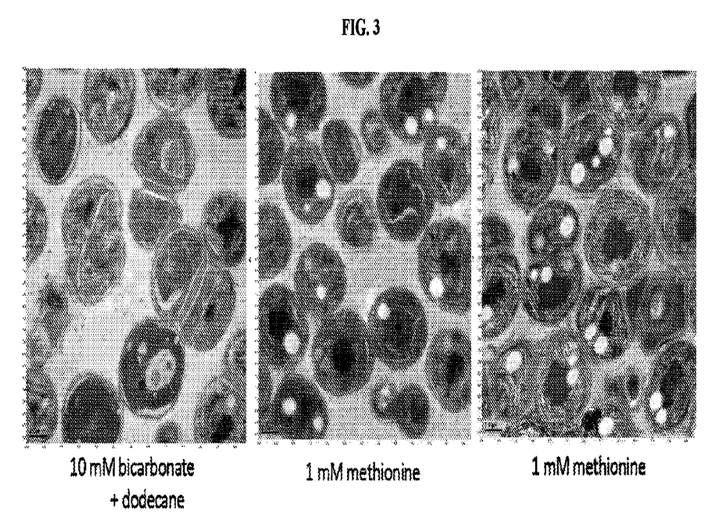
FIG. 3 are images demonstrating methyl laurate accumulation in cyanobacteria.
Figure 4A:
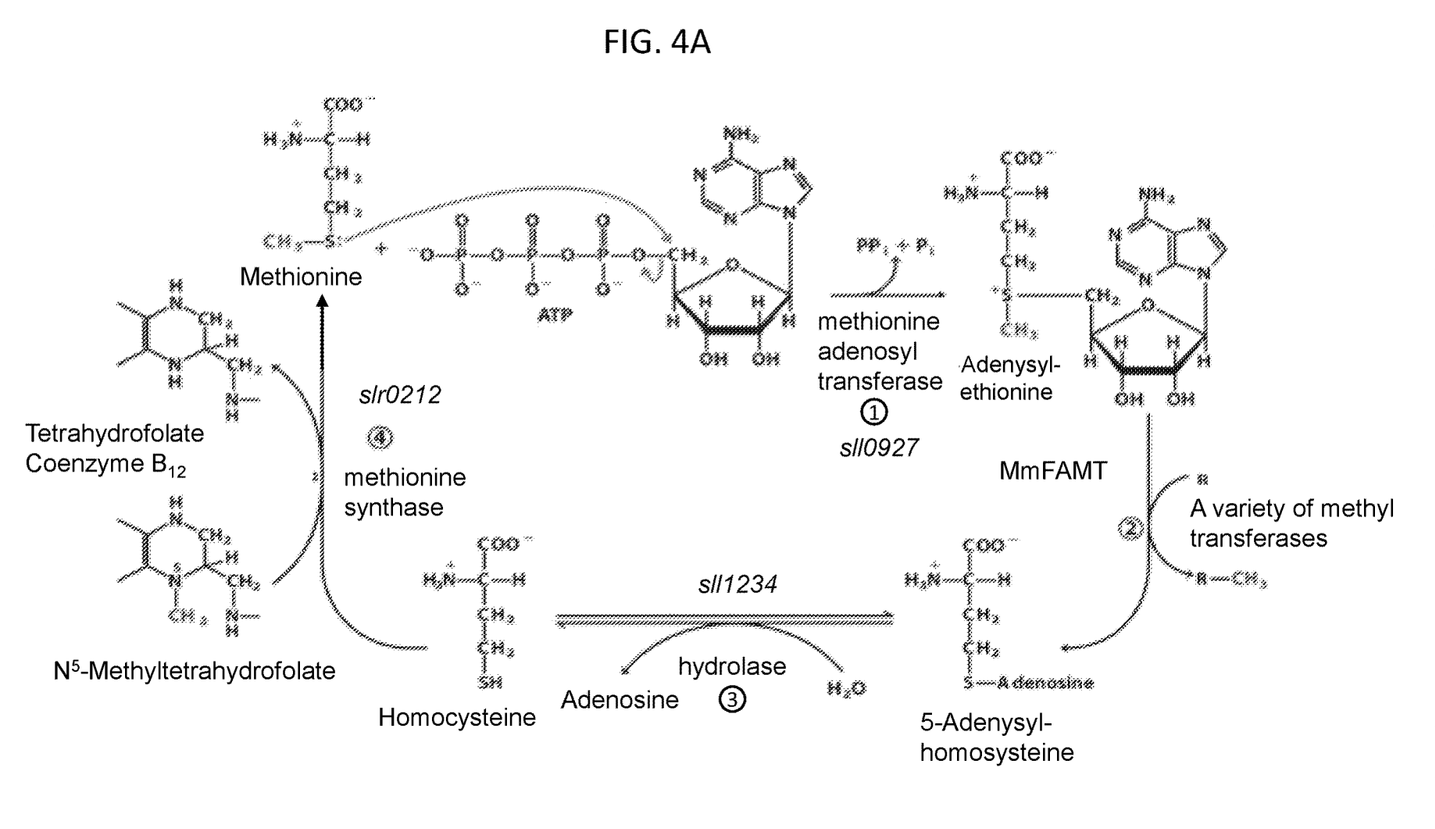
Figure 4B:
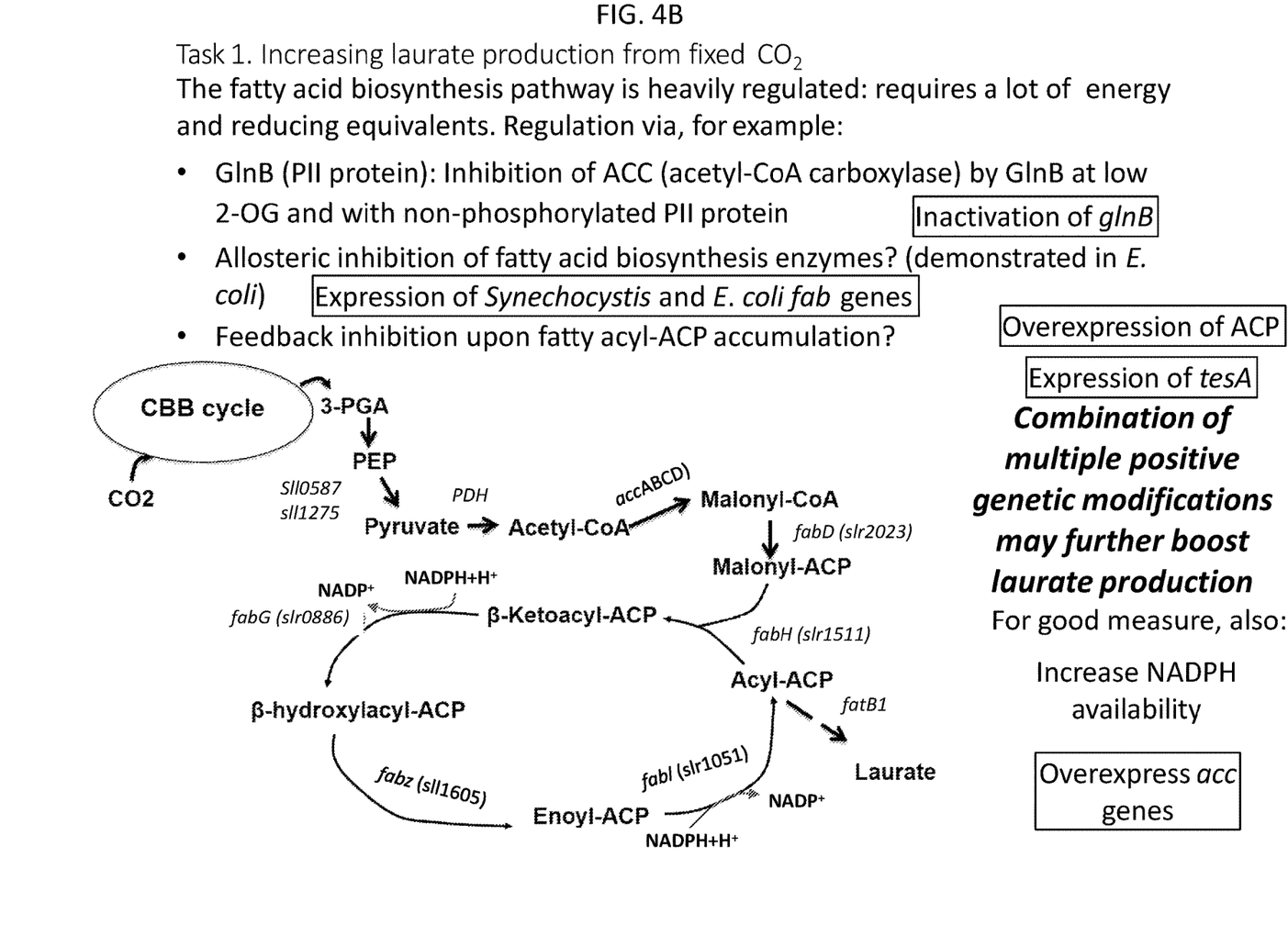
(FIG. 4B) a schematic representation of various strategies adopted to increase laurate production from fixed $CO_2$.
Figure 4C:
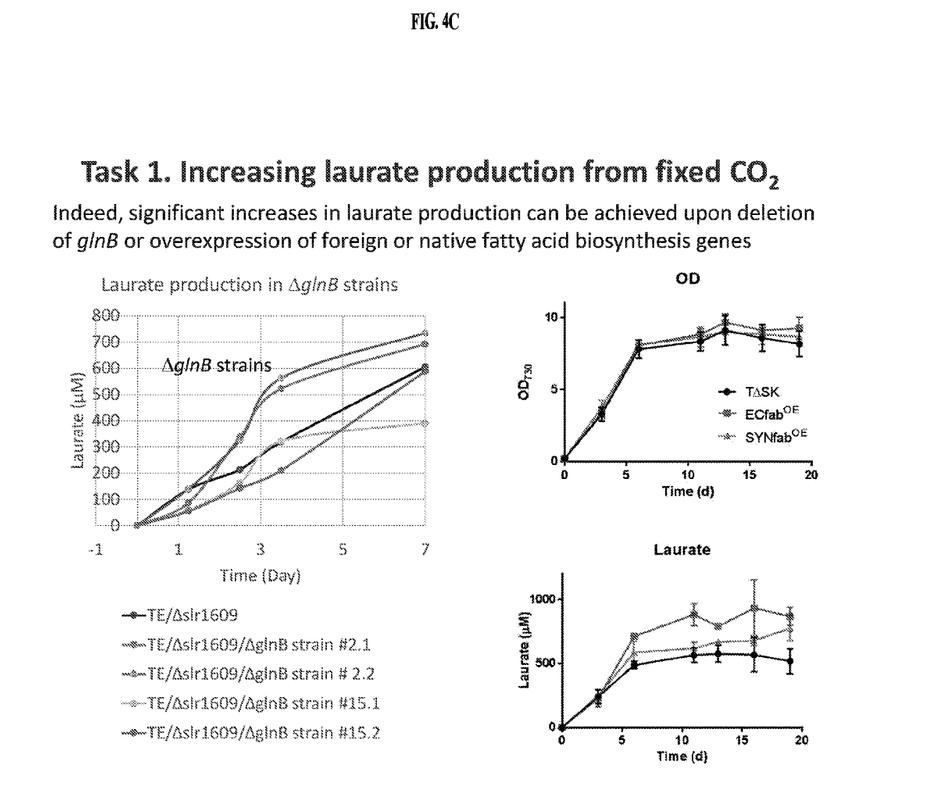
(FIG. 4C) graphs demonstrating increased laurate production upon deletion of nitrogen regulatory protein P-II, GlnB, or overexpression of foreign or native fatty acid biosynthesis genes. Acetyl-CoA carboxylase (ACC) can be inhibited by disrupting GlnB protein. Other approaches include, for example, allosteric inhibition of fatty acid biosynthesis enzymes, which has been demonstrated in *E. coli*, and/or feedback inhibition to promote acyl-ACP accumulation. Additionally, a combination of multiple positive genetic modifications may further boost laurate production.
Figure 5:
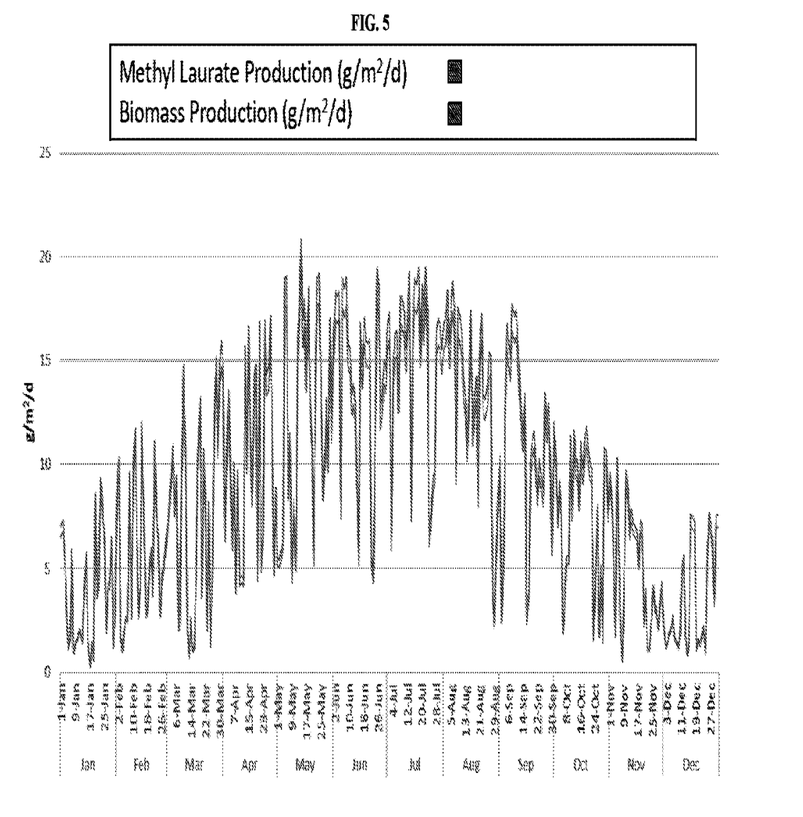
FIG. 5 presents an annual production simulation, assuming about equal productivity of biomass and methyl laurate, for techno-economic analysis of methyl laurate production. Production of biomass and methyl laurate is hourly estimated as a fraction of this energy and dependent on pond biomass density (g/L). Peak productivity corresponds to roughly 38 $g/m^2/d$ of only biomass.

Cyanobacteria were initially genetically modified to produce free fatty acids and fatty acyl esters. As stable ethyl laurate production was elusive, alternatives such as use of a fatty acid methyl transferase (FAMT) having activity toward laurate were considered. See FIG. 1. The FAMT gene derived from *Mycobacterium marinum* was amplified by PCR and integrated into a plasmid with *Synechocystis* flanking regions, thus targeting the gene for integration into a specific site on the *Synechocystis* genome. An antibiotic-resistance marker was integrated in the same plasmid to allow for transformant selection. In this example, the host strain was previously engineered to produce laurate by incorporation of a thioesterase gene, along with other mutations. The host strain with the inserted methylase gene is able to synthesize methyl laurate. As shown in FIG. 2A, the addition of catalytic amounts of methionine, a precursor for S-adenosylmethionine (SAM), helped methyl laurate yield. In some cases, methyl laurate production required the addition of about 0.25 mM methionine. As shown in FIG. 2B, laurate levels were depleted as methyl laurate accumulated. As shown in FIG. 3, methyl laurate accumulated in cyanobacteria.

Together, these data demonstrate development of a genetically modified cyanobacteria strain that efficiently converts free fatty acids to methyl esters. These data further demonstrates that ethyl laurate production suppresses laurate accumulation, and that methyl laurate production requires addition of catalytic amounts (e.g., approximately 0.25 mM) amounts of methionine. Advantageously, the methods described herein eliminate the requirement for an appropriate stoichiometry of produced ethanol and laurate.

These data further demonstrate successful photosynthetic production of methyl laurate at competitive yields in a cyanobacterium, with concomitant reduction in laurate levels. This demonstrates the capability of transformable cyanobacterial systems to produce excreted drop-in biodiesel from $CO_2$, water and light.

I claim:

1. A genetically engineered *Synechocystis* sp. PCC 6803 cyanobacterium, wherein the engineered cyanobacterium has been transformed with one or more plasmid vectors comprising (i) an expression cassette comprising a first nucleotide sequence encoding a *Mycobacterium marinum* fatty acid methyl transferase (FAMT) and (ii) a second nucleotide sequence encoding a thioesterase, wherein the genetically engineered cyanobacterium includes an inactivated nitrogen regulatory protein P-II gene, g1nB, and wherein the genetically engineered cyanobacterium has an increased production of methyl laurate as compared to methyl laurate production by a native *Synechocystis* sp. PCC 6803 cyanobacterium.

2. The genetically engineered cyanobacterium of claim 1, further comprising one or more exogenous nucleotide sequences encoding an S-adenosylmethionine (SAM) regeneration enzyme.

3. A method of producing methyl laurate with a genetically modified cyanobacterium, the method comprising:

(a) introducing an expression cassette comprising a nucleic acid encoding a *Mycobacterium marinum* fatty acid methyl transferase (FAMT) into a cyanobacterium to obtain a genetically modified cyanobacterium comprising the expression cassette, wherein the genetically modified cyanobacterium further comprises an exogenous nucleotide sequence encoding a thioesterase, wherein the genetically engineered cyanobacterium includes an inactivated nitrogen regulatory protein P-II gene, g1nB, and wherein the genetically engineered cyanobacterium has an increased production of methyl laurate as compared to methyl laurate production by a native *Synechocystis* sp. PCC 6803 cyanobacterium, (b) culturing the genetically modified cyanobacterium in a culture under conditions in which the nucleic acid encoding the FAMT is expressed and the genetically modified cyanobacterium produces and excretes methyl laurate;

(c) contacting the culture with a dodecane layer, whereby methyl laurate collects in the dodecane layer; and (d) isolating methyl laurate from the dodecane layer.

4. The method of claim 3, wherein the culturing is in the presence of exogenous methionine.

5. The method of claim 3, wherein the genetically modified cyanobacterium is *Synechocystis* sp. PCC 6803.

6. A method of increasing fatty acid or fatty acyl ester production of a genetically modified strain of cyanobacterium, the method comprising:

(a) obtaining a genetically modified cyanobacterium, wherein the genetically modified cyanobacterium includes an inactivated nitrogen regulatory protein P-II gene g1nB; and (b) introducing into the genetically modified cyanobacterium a first nucleotide sequence encoding a FAMT and a second nucleotide sequence encoding a fatty acid Acyl-ACP thioesterase to produce a resulting genetically modified cyanobacterium exhibiting increased fatty acid or fatty acyl ester production relative to fatty acid or fatty acyl ester production of the genetically modified cyanobacterium which does not comprise the first nucleotide sequence.

7. The method of claim 6, wherein the FAMT is *Mycobacterium marinum*.

8. The method of claim 6, wherein the resulting genetically modified cyanobacterium further comprises one or more exogenous nucleotide sequences encoding an S-adenosyl methionine (SAM) regeneration enzyme.

9. The method of claim 6, further comprising culturing the resulting genetically modified cyanobacterium under conditions in which the first nucleic acid encoding FAMT is expressed and methyl laurate is produced and excreted from the genetically modified cyanobacterium.

10. The method of claim 6, further comprising culturing the resulting genetically modified cyanobacterium in the presence of exogenous methionine.

11. A genetically modified *Synechocystis* cyanobacterium strain comprising a first heterologous gene encoding a fatty acid methyl transferase (FAMT) and a second heterologous gene encoding a thioesterase, whereas the genetically modified *Synechocystis* cyanobacterium strain is capable of increased production of methyl laurate compared to an unmodified *Synechocystis* cyanobacterium strain not comprising the first heterologous gene, wherein the genetically modified *Synechocystis* cyanobacterium includes an inactivated nitrogen regulatory protein P-II gene, g1nB.

12. The strain of claim 11, wherein the strain is *Synechocystis* sp. PCC 6803.

\* \* \* \* \*